United States Patent

Kobayashi et al.

[11] Patent Number: 5,998,489
[45] Date of Patent: Dec. 7, 1999

[54] METHANOL PREPARATION PROCESS

[75] Inventors: Kazuto Kobayashi, Hiroshima; Hideaki Nagai, Tokyo, both of Japan

[73] Assignees: Mitsubishi Heavy Industries, Ltd.; Mitsubishi Chemical Company, Inc., both of Tokyo, Japan

[21] Appl. No.: 09/118,043

[22] Filed: Jul. 17, 1998

[51] Int. Cl.$^6$ .................................................. C07C 27/00
[52] U.S. Cl. .......................... 518/704; 518/700; 518/702; 518/728
[58] Field of Search ....................... 518/704, 702, 518/728, 700

[56] References Cited

U.S. PATENT DOCUMENTS

| | | | |
|---|---|---|---|
| 4,238,403 | 12/1980 | Pinto | 260/449.5 |
| 4,455,394 | 6/1984 | Pinto | 518/704 |
| 5,063,250 | 11/1991 | Murayama et al. | 518/704 |

FOREIGN PATENT DOCUMENTS

| | | | |
|---|---|---|---|
| 0 040 481 A2 | 11/1981 | European Pat. Off. | C07C 31/04 |
| 55-139492 | 10/1980 | Japan . | |
| 60-245997 | 12/1985 | Japan . | |
| 1-180841 | 7/1989 | Japan . | |
| 2 213 817 | 8/1989 | United Kingdom | C07C 27/20 |

*Primary Examiner*—Paul J. Killos
*Assistant Examiner*—J. Parsa
*Attorney, Agent, or Firm*—Myers Bigel Sibley & Sajovec, P.A.

[57] ABSTRACT

Provided is a methanol production process from hydrocarbon which lessens generation of waste water and reduces boiler water. Specifically, there are provided a methanol production process comprising the steps of (a) reacting hydrocarbon with steam to generate a synthesis gas containing hydrogen, carbon monoxide and carbon dioxide as main components, (b) reacting the synthesis gas on a methanol synthesis catalyst and recovering crude liquid methanol, and (c) distilling the recovered crude methanol into refined methanol and waste water, wherein the hydrocarbon comes in contact with the waste water neutralized with alkali metal salt or the like at the step (c) so as to be humidified, and comes in contact with condensed water separated from the synthetic gas obtained at the step (a) so as to be further humidified, and is then supplied to the step (a).

2 Claims, 2 Drawing Sheets

METHANOL PREPARATION PROCESS

BACKGROUND OF THE INVENTION

1. Field of the Invention

The present invention relates to a methanol production process starting from hydrocarbon, and more particularly to an improved methanol production process which lessens generation of waste water and saves the amount of boiler feed water.

2. Description of the Related Art

For example, Japanese Patent Provisional Publication No. 1-180841/1989 discloses that a process for producing methanol from hydrocarbon, generally consists of the following steps:

(1) a synthesis gas preparation step wherein steam is reacted with gaseous hydrocarbon or vaporized hydrocarbon liquid on a nickel-based catalyst at a temperature of 800 to 1000° C. in a reforming furnace, thereby preparing synthetic gas containing hydrogen, carbon monoxide and carbon dioxide as main components;

(2) a synthesizing step wherein the synthesis gas is reacted on a copper-based catalyst at a pressure of 50 to 150 atm and a temperature of 200 to 300° C., and the resulting crude liquid methanol is separated from the reacted gas; and (3) a distilling step wherein the crude liquid methanol is distilled through one or more distillation columns, thereby separating refined methanol from waste water containing one or more organic compounds having lower boiling points than that of methanol (hereinafter referred to as lower b.p. organic compounds), and one or more organic acids as well as one or more organic compounds having higher boiling points than that of the methanol (hereinafter referred to as higher b.p. organic compounds).

In the synthesis gas preparation step, usually, it is necessary to supply steam having the three times moles of the number of carbons of hydrocarbon used as a starting material. For example, 3 m$^3$ of H$_2$O is added for 1 m$^3$ of CH$_4$. Thus, a large amount of steam is required for preparing methanol synthesis gas. By utilizing heat generated at each preparation step, steam is recovered from water having a high purity so as to be used for a process.

In the synthesizing step, methanol is produced from carbon monoxide and hydrogen in the synthesis gas, while methanol and water are generated from carbon dioxide and hydrogen. The water and some impurities are contained, together with the methanol, in the crude liquid methanol, and are separated at the next distillation step. The separated water is discharged from the system without being utilized further.

Japanese Patent Provisional Publications Nos. 51-115505/1976, 55-139492/1980, 60-245997/1985, 57-18640/1982, and 1-180841/1989 disclose process for reducing the amount of steam required for the conventional synthesis gas preparation process.

In the methanol production process described above, a large amount of expensive water with high quality is needed as boiler water. Since the water separated in the distillation step contains the following components and can be hardly utilized, it is discarded as it is.

(a) a large number of higher b.p. organic compounds. For example, higher alcohol having a carbon number of 2 or more and paraffins having a carbon number of 14 to 60.

(b) organic acid salt and ester such as those of formic acid.

(c) alkali metal salt.

The organic acid salt and ester have high acidity and corrosivity. For this reason, for example, alkali metal hydroxide such as sodium hydroxide, or carbonate such as sodium carbonate is added for neutralization. Consequently, alkali metal salt is contained in waste water in the distillation step as described in the Japanese Patent Provisional Publication No. 57-18640/1982.

It is extremely difficult to remove these impurities from the waste water obtained in the distillation step, and a great deal of cost is required to utilize the waste water as boiler water for a methanol production process. Therefore, the waste water is discarded without being further utilized.

Furthermore, since the waste water contains the said components, it is hazardous to the public and needs to be subjected to a waste water treatment such as a biological treatment.

Thus, the waste water obtained in the distillation step contains a large number of organic compounds and the like and should be subjected to the waste water treatment. For this reason, a great deal of cost is required. If the waste water can be utilized for the process, the required amount of the expensive boiler water can be reduced. Therefore, it has been desired that the waste water should be recycled.

The present inventors disclose a process for process steam reduction, being performed at a process in which an alkali metal compound is not added in the distillation step as described in the Japanese Patent Provisional Publication No. 1-180841/1989. In this process, stainless materials having nickel and chromium are placed for materials of a distillation column and a hydrocarbon humidifier. The amount of waste water to be supplied is set to 1/10 to 1/20 as much as that for a conventional process in order to prevent the concentration of organic acid from increasing in the humidifier. Thus, corrosion of the material caused by the organic acid can be avoided and the waste water can be utilized.

According to the above-mentioned process, while the amount of the waste water can be decreased and the boiler water can be reduced, cost is increased because stainless steel having a higher grade than carbon steel is used for materials of the humidifier and the distillation column.

SUMMARY OF THE INVENTION

In order to solve the above-mentioned conventional problems, it is an object of the present invention to provide a process for humidifying hydrocarbon and reducing steam for the process, that is, reducing expensive boiler water by utilizing waste water obtained in a distillation step. It is because the waste water, which alkali metal salt has been contained in, is desired to be recycled.

The present invention provides:

(1) a process for producing methanol from hydrocarbon comprising the steps of (a) reacting hydrocarbon with steam to generate synthesis gas containing hydrogen, carbon monoxide and carbon dioxide as main components, (b) reacting the synthesis gas on a catalyst for methanol synthesis and recovering crude liquid methanol from the reacted gas, and (c) distilling the crude methanol into refined methanol and waste water containing lower b.p. organic compounds, higher b.p. organic compounds and organic acids, wherein the hydrocarbon comes in contact with the waste water which has been neutralized with alkali metal salt or hydroxide in the step (c) so as to be humidified, and comes in contact with condensed water separated from the synthesis gas obtained in the step (a) so as to be further humidified, and is then supplied to the step (a); and (2) As one of the preferred embodiments for (1), the process for preparing methanol synthesis gas from hydrocarbon, wherein when the hydrocarbon comes in contact with the waste water which has been neutralized with the alkali metal salt or hydroxide at the step (c) so as to be humidified, the hydrocarbon preheated to a temperature of 250 to 430° C. adiabatically comes in contact with the waste water so as to be humidified.

In the methanol production process according to the present invention, the waste water obtained in the distillation step, which has not conventionally been utilized but discharged, is effectively used. Consequently, the following advantages can be obtained.

(1) The amount of the waste water obtained in the distillation step, which is occupying most of the waste water yielded in the methanol production process, may be decreased. Thus, a load for a waste water treatment may be considerably reduced.

(2) The used amount of the boiler water having a high purity may be decreased.

(3) While the waste water obtained in the distillation step is supplied to a primary humidifier and condensed water obtained from the synthetic gas is supplied to a secondary humidifier, a hydrocarbon gas is humidified. Thus, mist contained in the hydrocarbon that has been humidified in the primary humidifier is washed with the condensed water supplied to the secondary humidifier, where the mist having contained sodium salt and sodium hydroxide in the primary humidifier is removed, and the sodium hydroxide in the mist is neutralized with carbonic acid contained in the condensed water. Consequently, a material for a preheater, a reactor or the like is hardly corroded at higher temperature.

(4) Preheating hydrocarbon to a temperature of 250 to 430° C. and employing an adiabatic type of primary humidifier may reduce the size of the plant further and cut down the cost still more.

DETAILED DESCRIPTION OF THE PREFERRED EMBODIMENTS

Figure 1:
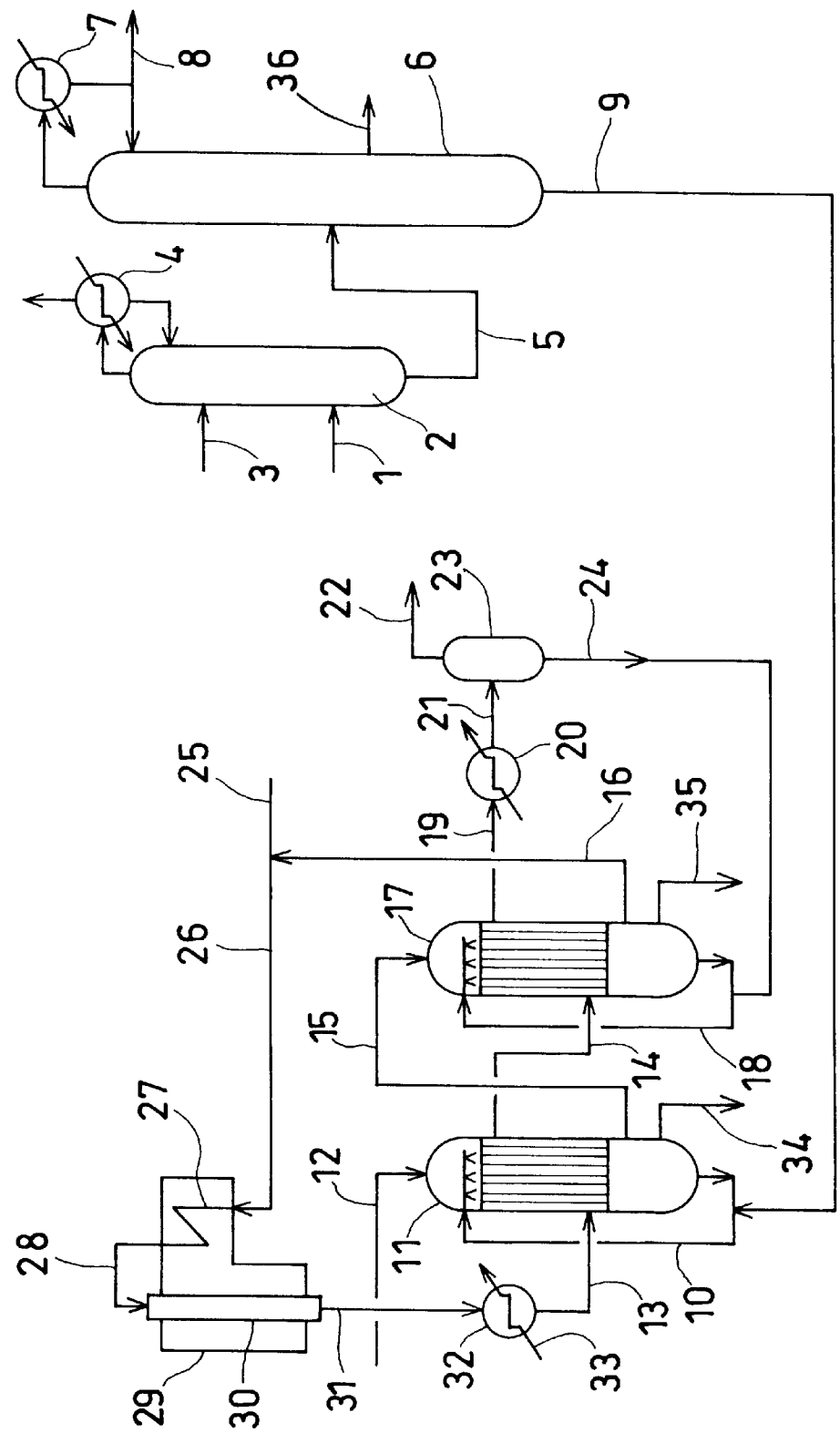
FIG. 1 is a diagram showing an example of a methanol production process according to the present invention.

In the present invention, a process for producing methanol from hydrocarbon can use, for example, the steps described in the above-mentioned Japanese Patent Provisional Publication No. 1-180841/1989. That is, the following steps can be used:

(1) a synthesis gas preparation step wherein steam is reacted with gaseous hydrocarbon or vaporized hydrocarbon liquid on a nickel-based catalyst at a temperature of 800 to 1000° C. in a reforming furnace (synthesis gas preparation furnace), thereby preparing a synthetic gas containing hydrogen, carbon monoxide and carbon dioxide as main components;

(2) a synthesizing step wherein the synthesis gas is reacted on a copper-based methanol synthesis catalyst at a pressure of 50 to 150 atm and a temperature of 200 to 300° C., and the produced crude liquid methanol is recovered from the reacted gas; and (3) a distillation step wherein the crude methanol is distilled through one or more distillation columns into refined methanol and waste water containing lower b.p. organic compounds, and higher b.p. organic compounds.

The starting hydrocarbon, according the present invention, includes gas such as natural gas, and liquid such as liquefied petroleum gas (LPG), naphtha and light oil.

In the reaction between hydrocarbon and steam there may be a case where a purge gas obtained at the synthesizing step is used for a part of the starting material together with the hydrocarbon, a case where carbon dioxide is added to the starting material together with the steam, or a case where oxygen containing gas is added to perform partial oxidation.

In the synthesis gas preparation step, a synthesis gas containing hydrogen, carbon monoxide and carbon dioxide as main components is prepared.

In the distillation step, a two-column process is generally used. Crude methanol obtained at the synthesizing step is supplied to a first distillation column, gases dissolving such as lower b.p. organic compounds, carbon dioxide and the like are separated from a top of the first distillation column. Methanol, water and higher b.p. organic compounds containing organic acid are obtained from a bottom of the first distillation column and supplied to a second distillation column. Refined methanol is separated from a top of the second distillation column and the higher b.p. organic compounds containing the organic acid and water are separated from the bottom of the second distillation column. Furthermore, separation process by one distillation column or by three or more distillation columns may be also performed.

In the present invention, waste water containing one or more higher b.p. organic compounds and organic acid salt, which will come in contact with hydrocarbon gas, may be separated from the bottom of the second distillation column according to the two-column process, or separated from a bottom or bottoms of one or more distillation columns according to the separating process of one column or three or more columns.

Although a humidifier used for the present invention is not particularly restricted, a heat-exchanger type humidifier for heating and vaporizing water at the same time is used favorably in respect of cost as described in the Japanese Patent Provisional Publication No. 55-139492/1980.

The crude methanol obtained at the synthesizing step contains methyl formate as a side reaction product. It produces formic acid by hydrolysis according to the following formula, which causes an apparatus to be corroded.

$$HCOOCH_3 + H_2O \rightleftharpoons CH_3OH + HCOOH \qquad \text{Formula (1)}$$

In order to prevent the corrosion, an alkali is usually added near a crude methanol feed supply stage of the first distillation column. Alkali metal carbonate or hydroxide may be usually used for the alkali. Examples of the alkali metal carbonate include sodium carbonate, potassium carbonate and the like. Examples of the alkali hydroxide include sodium hydroxide, potassium hydroxide and the like. In particular, the sodium hydroxide may be preferably used in respect of effects and cost.

Formic acid is neutralized by addition of the sodium hydroxide so that sodium formate is obtained through the following formula.

$$HCOOH + NaOH \rightleftharpoons HCOONa + H_2O \qquad \text{Formula (2)}$$

For this reason, the waste water obtained at the distillation step contains such sodium salt and unreacted sodium hydroxide. Consequently, it is difficult to utilize the waste water.

The hydrocarbon is humidified so that heat sources having a low temperature of 150 to 300° C. in the synthesis gas preparation step and the synthesizing step can effectively be utilized and steam for the process is reduced. Therefore, the application of the hydrocarbon humidification has been investigated as described above.

If the waste water obtained in the distillation step is utilized for the hydrocarbon humidification, mist of gas discharged from the humidifier also entrains the alkali metal hydroxide because the waste water contains the unreacted alkali metal hydroxide as described above. Since the mist adheres to a preheater and a reformer tube, alkali corrosion takes place. Although the adhered amount of the alkali metal hydroxide is very small, it becomes a serious disadvantage because of continuous operation of a methanol synthesis gas preparation process for a long period.

Consequently, it has been proposed that an organic alkali is used in place of the alkali metal hydroxide. Various kinds of organic alkali (for example, amines) are decomposed into harmless gases by a nickel-based catalyst at the synthesis gas preparing step. Since the organic alkali generally produce small effects of neutralization, however, the amount of the organic alkali to be used is increased. In addition, the organic alkali is more expensive than an inorganic alkali. Thus, the organic alkali is not practically suited.

In the present invention, the hydrocarbon is humidified in the following manner. The hydrocarbon first comes in contact with the waste water obtained from the distillation step, and then with condensed water separated from a synthetic gas. Therefore, mist entrained in the hydrocarbon during humidification with the waste water is washed with the condensed water. At the same time, alkali metal hydroxide contained in the mist is neutralized with carbonic acid dissolved in the condensed water so that alkali metal carbonate is formed. Consequently, the mist of the condensed water entrained in the hydrocarbon contains a very small amount of alkali metal carbonate.

There is a possibility that the alkali metal carbonate might adhere and deposit onto tubes of a natural gas preheater provided on the downstream of the humidifier. However, the preheater has a low metal surface temperature which is less than 600° C. In addition, an ambient medium is also a mixed gas of hydrocarbon and steam, containing the steam which is having the three times moles of the number of carbons of the hydrocarbon. Therefore, a carbon may be rarely deposited by thermal decomposition of the hydrocarbon, and high temperature corrosion caused by the alkali metal carbonate in the preheater may be prevented.

Furthermore, conventional carbon steel can be used for materials of the humidifier and the distillation column.

According to the present invention, the following mode can also be used. Hydrocarbon preheated to a temperature of 250 to 430° C. adiabatically comes in contact with waste water containing alkali metal salt or hydroxide so as to be humidified. Thereafter, the hydrocarbon is further humidified with the condensed water by using a heat-exchanger type humidifier.

The hydrocarbon is preheated to the temperature of 250 to 430° C. for removal of sulfur compounds contained in the hydrocarbon before it is supplied to the humidifier.

In an adiabatic humidifier, the waste water or the like may be sprayed for adiabatic contact. A packed column is preferably provided to increase a contact efficiency as described, for example, in the Japanese Patent Provisional Publication No. 60-245997/1985.

Since the adiabatic humidifier is used, tubes for heat exchanging can be omitted as described in the Examples below. A size of a synthesis gas preparation apparatus can also be reduced and the cost of the plant can be cut down.

The present invention will be described in more detail with reference to Example 1 shown in FIG. 1.

EXAMPLE 1

In FIG. 1, crude methanol obtained in a synthesizing step is supplied through a passage 1 to an intermediate stage of a first distillation column 2. Furthermore, a small amount of water is sometimes injected through a passage 3. Lower b.p. organic compounds are concentrated on a top of the first distillation column 2, and is partially condensed and refluxed by a condenser 4. The rest of the lower b.p. organic compounds are discharged to the outside of a system together with a dissolved gas.

Methanol and water mainly occupying a bottom of the first distillation column 2 are supplied through a passage 5 to an intermediate stage of a second distillation column 6. On a top of the second distillation column 6, cooling is performed by a condenser 7 for condensation so as to refine methanol by a reflux. Consequently, a product methanol having a high purity is extracted through a passage 8 to the outside of the system. The water mainly occupies a bottom of the second distillation column 6, and contains a small amount of the higher b.p. organic compounds, organic substances and a very small amount of inorganic substances originated in an apparatus. The higher b.p. organic compounds may be discharged out of the system through a passage 36 at a certain stage of the second distillation column 6 for subsequent treatments such as incineration.

In a conventional process, alkali metal hydroxide or the like is supplied to the first distillation column 2. And since a fluid obtained from the bottom of the first distillation column 2 contains alkali metal salt or hydroxide, the fluid is discharged as waste water to the outside of the system. Although a reboiler or the like is each provided on the first distillation column 2 and the second distillation column 6, such reboilers are not directly related to the present explanation and are not shown.

The waste water supplied from the bottom of the second distillation column 6 is fed through a passage 9, and then through a circulating water passage 10 of a primary humidifier 11, to a top of the primary humidifier 11.

The primary humidifier 11 is of a heat-exchanger type. A preheated starting material hydrocarbon gas is introduced through a passage 12, and comes in contact with the waste water. The hydrocarbon gas is also heated and humidified with a synthetic gas having a high temperature which is introduced through a passage 13. The synthetic gas whose heat is recovered by the primary humidifier 11, is then discharged through a passage 14 and is supplied to a secondary humidifier 17. The humidified hydrocarbon enters through a passage 15 to the secondary humidifier 17.

Condensed water from the synthesis gas is introduced through passage 24 and then through a circulating water passage 18 to a top of the secondary humidifier 17. The secondary humidifier 17 is also of a heat-exchanger type. The synthesis gas introduced through the passage 14 is heat recovered, and is discharged through a passage 16. Then, steam necessary for the process is added to the hydrocarbon gas through a passage 25. Thereafter, the hydrocarbon and steam mixture gas is supplied through a passage 26, through a preheater 27 provided on a convection portion of a reforming furnace (synthetic gas preparation furnace) 29, and through a passage 28, into a reformer tube 30 filled with a nickel-based catalyst.

The synthesis gas supplied from the reaction tube 30 passes through a passage 31, heats the boiler water fed through a passage 33 by means of a heat exchanger 32 so as to generate high-pressure steam, and is then supplied into the primary humidifier 11 through the passage 13. A part of the concentrated waste water is discharged through a passage 34 to the outside of the system, while a part of concentrated condensed water is discharged through a passage 35 to the outside of the system. A part of the condensed water discharged from the secondary humidifier 17 may be supplied through the passage 35 and then through the circulating water passage 10 to the primary humidifier 11.

The synthesis gas discharged from the secondary humidifier 17 passes through a passage 19 and is cooled by a heat exchanger 20 into the passage 21. The condensed water is separated by means of a gas-liquid separator 23 and is discharged through a passage 22. The condensed water is introduced through the passage 24, and then through the circulating water passage 18 into the secondary humidifier 17.

Table 1 shows a main composition of the waste water in the passage 9 from the distillation step.

TABLE 1

Example of Composition of Waste Water from Distillation Step

| | |
|---|---|
| $H_2O$ | 99.98% by weight |
| Sodium Formate | 100 ppm |
| Sodium Hydroxide | 6 ppm |
| $CH_3OH$ | 100 ppm |
| $C_2H_5OH$ | 2 ppm |

Table 2 shows a main composition of the concentrated condensed waste water in the passage 35. At this time, the amount of the waste water discharged from the primary humidifier 11 was 1/10 of a flow amount of the passage 9.

TABLE 2

Example of Comp. of Waste Water from Secondary Humidifier

| | |
|---|---|
| $H_2O$ | 99.99% by weight |
| Sodium Formate | 1 ppm |
| Sodium Carbonate | 0.08 ppm |

As described above, there are two humidifiers. The waste water obtained from the distillation step is supplied to a primary humidifier, while the condensed water obtained from the synthetic gas is supplied to a secondary humidifier so as to humidify hydrocarbon. Consequently, mist entrained in the hydrocarbon gas which has been humidified in the primary humidifier is washed with the condensed water supplied to the secondary humidifier so that the mist containing sodium salt and sodium hydroxide which is supplied from the primary humidifier is removed and the sodium hydroxide contained in the mist is neutralized with carbonic acid contained in the condensed water.

Furthermore, the circulating water in the secondary humidifier has a low sodium salt concentration. Therefore, the amount of the sodium salt, contained in the mist entrained by the humidified hydrocarbon gas flowing out of the secondary humidifier, is greatly reduced.

Thus, high temperature corrosion of a preheater material or a reactor material hardly takes place.

EXAMPLE 2

A second example of the present invention will be described in more detail with reference to FIG. 2.

Figure 2:
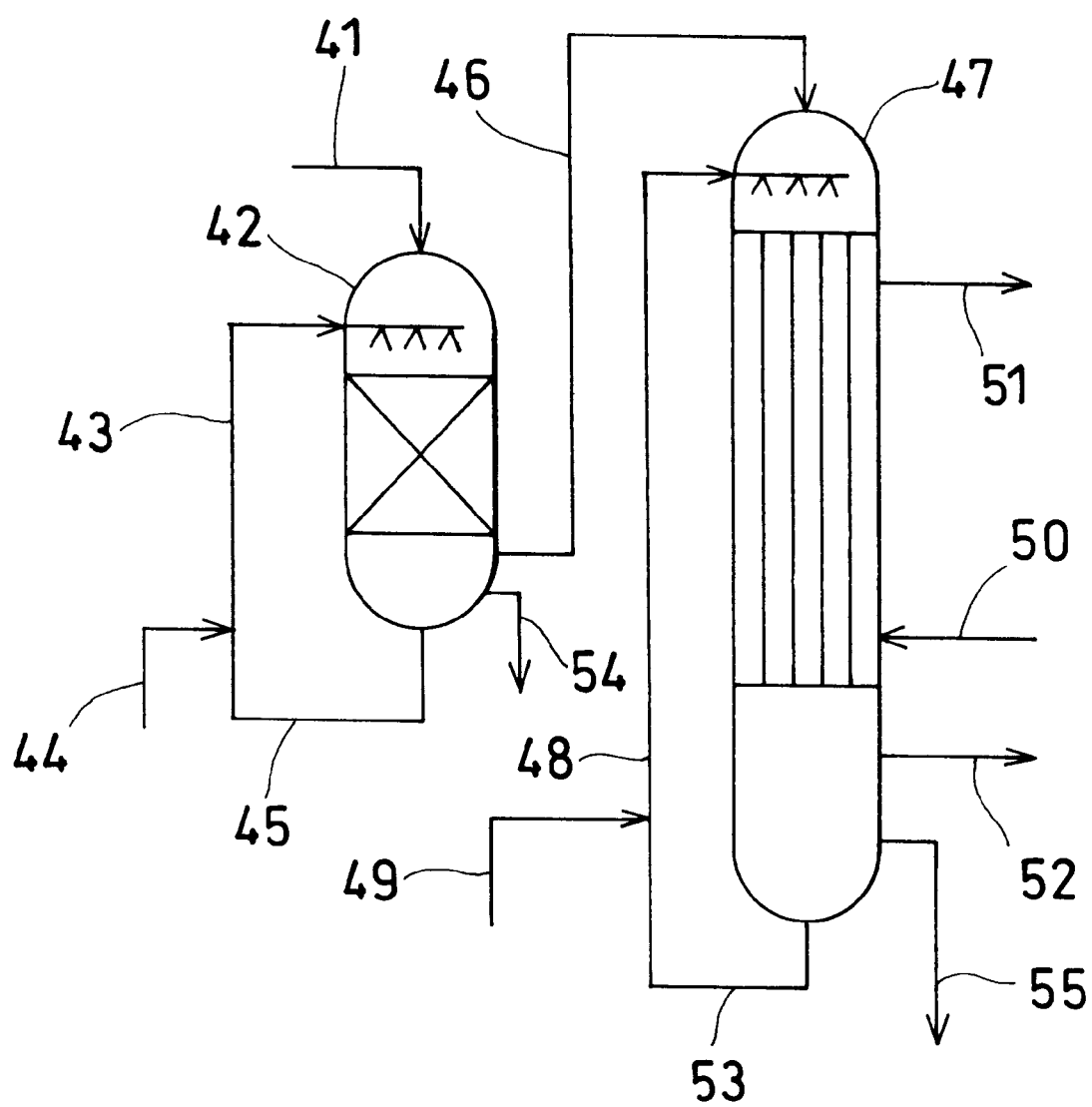
FIG. 2 shows a case where the primary humidifier in FIG. 1 is replaced with an adiabatic humidifier.

FIG. 2 is a diagram showing a case where an adiabatic humidifier is used in place of the primary humidifier in FIG. 1 and waste water obtained from the distillation step is treated at a low temperature.

A hydrocarbon gas heated to a temperature of 250 to 430° C. is introduced into an adiabatic humidifier 42 through a passage 41, and comes in contact with the waste water from the distillation step through a circulating water passage 43 so as to be humidified. The adiabatic humidifier 42 is provided with a packed bed to increase a contact efficiency. The waste water which has not been evaporated in the adiabatic humidifier 42 is discharged through a passage 45 to the outside of the humidifier for circulation. The waste water from the distillation step is supplied from a passage 44 to the circulating water passage 43. The concentrated waste water is discharged through a passage 54 to the outside of the system.

The hydrocarbon humidified by the adiabatic humidifier 42 is introduced into a heat-exchanger type humidifier 47 through a passage 46. In the heat-exchanger type humidifier 47, condensed water obtained from a synthesis gas is supplied through a passage 49, and through a passage 48 to an upper portion of the heat-exchanger type humidifier 47 together with the water fed from a circulating water passage 53 to further humidify the hydrocarbon. The humidified hydrocarbon is introduced into a gas reforming furnace (synthesis gas preparation furnace) through a passage 52. In the same manner as in FIG. 1, the synthetic gas obtained after high-pressure steam is recovered is used as a heat source of the heat-exchanger type humidifier, and is introduced through a passage 50 and is heat recovered, and is then fed to a next step through a passage 51. A part of the condensed water obtained from the synthetic gas, which is concentrated by the heat-exchanger type humidifier 47, is discharged through a passage 55 to the outside of the system. The water supplied through the passage 55 can also be returned to the passage 44. Also in the present system, almost the same result as the compositions of the waste water shown in Tables 1 and 2 according to Example 1 was obtained.

In addition to the effects described in Example 1, the present system produces the following effects. The first humidifier described in Example 1 is not of a heat-exchanger type but of an adiabatic type. Therefore, tubes for heat exchanging can be omitted, a size of a synthesis gas preparation apparatus can be reduced and cost of a plant can be cut down.

We claim:

1. A process for producing methanol from hydrocarbon comprising the steps of:

(a) reacting hydrocarbon with steam to generate a synthesis gas containing hydrogen, carbon monoxide and carbon dioxide as main components;

(b) reacting said synthesis gas on a methanol synthesis catalyst and recovering crude liquid methanol from the reacted gas; and (c) distilling said recovered crude methanol into refined methanol and waste water containing lower boiling point organic compounds, higher boiling point organic compounds and organic acid, wherein the hydrocarbon comes in contact with the waste water which has been neutralized with alkali metal salt or hydroxide in the step (c) so as to be humidified, and then comes in contact with condensed water separated from the synthetic gas obtained in the step (a) so as to be further humidified, and is then supplied to the step (a).

2. A process for producing methanol from hydrocarbon according to claim 1, wherein when the hydrocarbon comes in contact with said waste water which has been neutralized with the alkali metal salt or hydroxide in the step (c) so as to be humidified, the hydrocarbon is preheated to a temperature of 250 to 430° C. and adiabatically comes in contact with said waste water.

* * * * *

UNITED STATES PATENT AND TRADEMARK OFFICE
CERTIFICATE OF CORRECTION

PATENT NO.     : 5,998,489
DATED          : December 7, 1999
INVENTOR(S)    : Kobayashi et al.

It is certified that error appears in the above-identified patent and that said Letters Patent is hereby corrected as shown below:

(On the Title Page)

[73] Assignees,       Second Assignee "Mitsubishi Chemical Company, Inc."
                      should read --Mitsubishi Gas Chemical Company, Inc.--.

Signed and Sealed this

Fifteenth Day of May, 2001

Attest:

NICHOLAS P. GODICI

*Attesting Officer*     Acting Director of the United States Patent and Trademark Office